Figure 1:
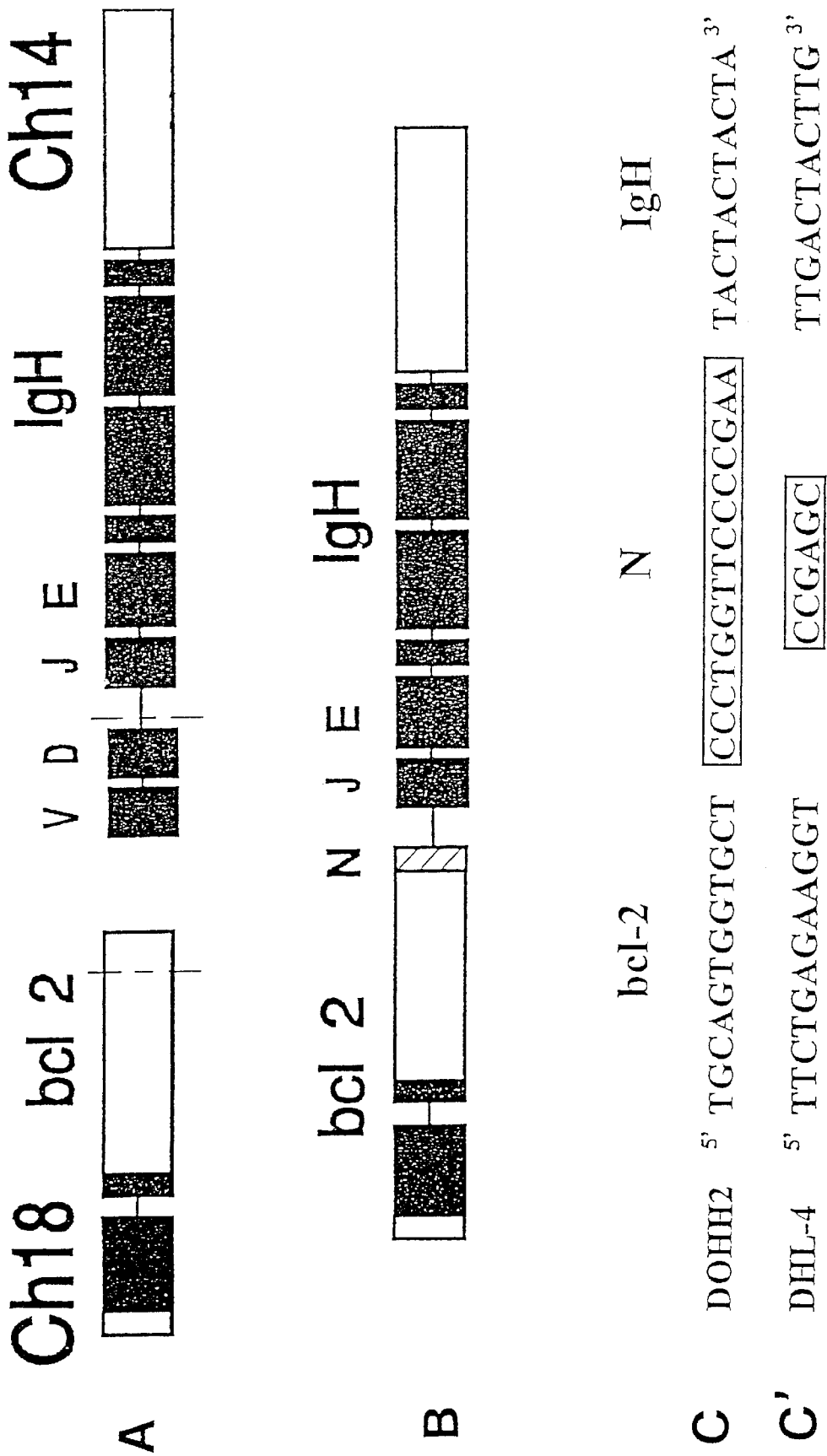

under barcode: US006005095A

United States Patent [19]
Capaccioli et al.

[11] Patent Number: 6,005,095
[45] Date of Patent: Dec. 21, 1999

[54] ANTISENSE TRANSCRIPT ASSOCIATED TO TUMOR CELLS HAVING A T(14;18) TRANSLOCATION AND OLIGODEOXYNUCLEOTIDES USEFUL IN THE DIAGNOSIS AND TREATMENT OF SAID TUMOR CELLS

[75] Inventors: Sergio Capaccioli, Florence; Susanna Morelli; Angelo Nicolin, both of Milan, all of Italy

[73] Assignee: Consiglio Nazionale Delle Ricerche, Rome, Italy

[21] Appl. No.: 08/894,784

[22] PCT Filed: Mar. 2, 1996

[86] PCT No.: PCT/EP96/00852

§ 371 Date: Dec. 15, 1997

§ 102(e) Date: Dec. 15, 1997

[87] PCT Pub. No.: WO96/27663

PCT Pub. Date: Sep. 12, 1996

[30] Foreign Application Priority Data

Mar. 3, 1995 [IT] Italy .................................. MI95A0420

[51] Int. Cl.⁶ .......................... C07H 21/04; C07H 21/02; A61K 48/00; C12Q 1/68
[52] U.S. Cl. ..................... 536/24.5; 536/23.1; 536/24.3; 536/24.31; 536/24.33; 514/44; 435/6; 435/91.1; 435/91.2
[58] Field of Search ............................. 435/6, 91.1, 91.2; 536/23.1, 24.3, 24.31, 24.33, 24.5; 514/44

[56] References Cited

U.S. PATENT DOCUMENTS 5,585,479  12/1996  Hoke et al. .............................. 536/24.5

FOREIGN PATENT DOCUMENTS

WO 92/22303  12/1992  WIPO .
WO 93/24653  12/1993  WIPO .

OTHER PUBLICATIONS

Tsujimoto et al, "Analysis of the structure, transcripts, and protein products of bcl–2, the gene involved in human follicular lymphoma", Proc. Natl. Acad. Sci 83:5214–5218, Jul. 1986.

Ohno et al, "Molecular analysis of a chromosomal translocation, t(9;14)(p13;q32) in a diffuse large cell lymphoma cell line expressing the Ki–1 antigen", Proc. Natl. Acad. Sci. 87:628–632, Jan. 1990.

Wasserman et al, "Vh gene rearrangement events can modify the immunoglobulin heavy chain during progression of B–lieage acute lymphoblastic leukemia", Blood 79(1):223–228, Jan. 1992.

Probst et al, "The G–tetrad in antisense targeting", Trends in Genetics 12(8):90–91, Aug. 1996.

Harris et al, "Strategies for targeted gene therapy", Trends in Genetics 12(10):400–405, Oct. 1996.

Marshall, "Gene Therapy's growing pains", Science 269:1050–1055, Aug. 1995.

Stein et al, "Problems in interpretation of data derived from in vitro and in vivo use of antisense oligodeoxynucleotides", Antisense Research and Development, 4:67–69, Jan. 1994.

Primary Examiner—Jeffrey Fredman
Attorney, Agent, or Firm—Oblon, Spivak, McClelland, Maier & Neustadt, P.C.

[57] ABSTRACT

A chimeric bcl-2/IgH antisense transcript that hybridizes with the pre-mRNA of a hybrid gene in t(14;18) translocated cells.

An ODN directed to complement any region of the above mentioned antisense transcript and the use thereof for diagnostic or therapeutic purposes.

14 Claims, 4 Drawing Sheets

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

CCCTGGTTCC CCGA                                            14

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

GTGCGTGGTT GATGGGGA                                   18

(2) INFORMATION FOR SEQ ID NO:3:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

CCCGAGTGAA G                                                11

(2) INFORMATION FOR SEQ ID NO:4:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:4:

CCCCGAATAC TACTACTA                                   18

(2) INFORMATION FOR SEQ ID NO:5:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:5:

TCCCTGGTTC CCCGAATA                                                        18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGAATACTAC TACTACTA                                                        18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ACTACTACGG TATGGACG                                                        18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TCCTCAGGTA AGAATGGC                                                        18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ACCATGTTCC GAGGGGAC                                                        18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GAGCCACATT TGGACGAG                                                        18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

AGTGATGGCT GAGGAATG                                                         18

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

CTGTCCAAGT ATTTGAAA                                                         18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

GGCTGGAAAG AGAACTGT                                                         18

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

GTGAGCAAAG GTGATCGT                                                         18

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

CTTCAAAACC ATTCTGAG                                                         18

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GGTCCGAGCT TGACTACT                                             18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGAGAAGGTC CGAGCTTG                                             18

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GGTGACCGTG GTCCCTTGCC CCCA                                      24

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GACCTTGTTT CTTGAAGGTT TCCTCGTCCC                                 30

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GCACCACTGC ATTTCAGGAA GACCCTGAAG                                 30

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GCGGGAAATC GTCGGTGACA TT                                                    22

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GATGGAGTTG AAGGTAGGGG TTTCGTG                                               27

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GACCTTGTTT CTTGAAGGTT TCCTCGTCCC                                            30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GCACCACTGC ATTTCAGGAA GACCCTGAAG                                            30

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TATTCGGGGA ACCAGGGA                                                         18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TAGTAGTAGT ATTCGGGG                                                         18

(2) INFORMATION FOR SEQ ID NO:27:
```

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

ATAAGCCCCT TGGTCCCT                                                        18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CGTCCATACC GTAGTAGT                                                        18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GCCATTCTTA CCTGAGGA                                                        18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

CGAACCGGGA TGGACTTC                                                        18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CTCGTCCAAA TGTGGCTC                                                        18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ACAGTTCTCT TTCCAGCC                                                        18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

GAGCAGGTTT ACACCGAG                                                        18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

ACGATCACCT TTGCTCAC                                                        18

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

CTCAGAATGC TTTTGAAG                                                        18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

AGCGATGGTC GTGTGAAA                                                        18

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

| | |
|---|---|
| AGTAGTCAAG CTCGGACC | 18 |

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

| | |
|---|---|
| CAAGCTCGGA CCTTCTCA | 18 |

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

| | |
|---|---|
| TCATCAGTTC GAGCCTGG | 18 |

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

| | |
|---|---|
| GTCCCCTCGG AACATGGT | 18 |

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

| | |
|---|---|
| AACCCCACTG AAAAAGATGA | 20 |

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

| | |
|---|---|
| ATCTTCAAAC CTCCATGATG | 20 |

(2) INFORMATION FOR SEQ ID NO:43:

```
      (i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:43:

GGTGACCGTG GTCCCTTGCC CCCAG                                                25

(2) INFORMATION FOR SEQ ID NO:44:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:44:

GCAATTCCGC ATTTAATTCA TGGTATTCAG GAT                                       33

(2) INFORMATION FOR SEQ ID NO:45:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:45:

AGTAGTCAAG CTCGGACC                                                        18

(2) INFORMATION FOR SEQ ID NO:46:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:46:

CAAGCTCGGA CCTTCTCA                                                        18

(2) INFORMATION FOR SEQ ID NO:47:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:47:

TCATCAGTTC GAGCCTGG                                                        18

(2) INFORMATION FOR SEQ ID NO:48:

(i) SEQUENCE CHARACTERISTICS:
          (A) LENGTH: 38 base pairs
          (B) TYPE: nucleic acid
          (C) STRANDEDNESS: single
          (D) TOPOLOGY: linear
```

```
    (ii) MOLECULE TYPE: DNA (xi) SEQUENCE DESCRIPTION: SEQ ID NO:48:

TGCAGTGGTG CTCCCTGGTT CCCCGAATAC TACTACTA                           38

(2) INFORMATION FOR SEQ ID NO:49:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

TTCTGAGAAG GTCCGAGCTT GACTACTTG                                    29
```

ANTISENSE TRANSCRIPT ASSOCIATED TO TUMOR CELLS HAVING A T(14;18) TRANSLOCATION AND OLIGODEOXYNUCLEOTIDES USEFUL IN THE DIAGNOSIS AND TREATMENT OF SAID TUMOR CELLS

This invention relates to an antisense transcript expressed in some kind of tumor cells and to synthetic oligodeoxynucleotides (ODN) useful in the diagnosis and treatment of said tumor cells.

More particularly, the present invention relates to an endogenous antisense transcript that complements the pre-mRNA (immature RNA) of the hybrid gene carrying the chromosome translocation t(14;18) that promotes the overexpression of BCL-2 protein, thus causing neoplastic transformation. The present invention relates also to oligodeoxynucleotides which inhibit the action of said transcript.

It is well known that the synthetic oligodeoxynucleotides are short single strand DNA chains. The nucleotide sequence is ordered in a specular fashion (antisense) to complement a nucleotide sequence within the mRNA to be inhibited. By that modality they are capable to regulate gene expression in a specific way.

It is important that the oligodeoxynucleotides have a proper length suitable to optimally hybridize the target mRNA. In general, the minimum length is of 10 bases and the maximum length is of about 100 bases. Preferably, the length is of 15–30 bases; still preferably it is of 18 bases since the statistical analysis teaches that every sequence having this length is unique within the human genome.

The oligodeoxynucleotides can act at different steps of the mRNA metabolic pathway, either at the nuclear or at the cytoplasmic level. It is moreover likely that oligodeoxynucleotides act at the ribosome level, or straight to the DNA level both in the nucleus and in the mitochondria. The nucleotide length of the oligodeoxynucleotides may be selected also in view of the basic knowledge of the person skilled in the art concerning the efficacy in the cellular membranes (Locke S. L. et al.: Mechanism of oligonucleotide uptake by cells: involvement of specific receptors? Proc. Natl. Acad. Sci. USA 86: 3474, 1989. Yakubov L. A. et al.: Characterization of oligonucleotide transport into living cells. Proc. Natl. Acad. Sci. USA 86: 6454, 1989).

It is also known that discrete regions within specific genes may be transcribed in both directions. More commonly, a single strand (positive) from the double strand is transcribed into mRNA and then translated into protein. In some circumstances, however, the negative strand may also be transcribed (endogenous antisense RNA), playing a regulatory role in the functions of the regular transcript. The antisense transcripts may regulate the synthesis, maturation, stability and translation of the messenger RNA (Green P. J. et al.: The role of antisense RNA in gene regulation, Ann. Rev. Biochem. 55: 569, 1990; Krystal G. W. et al.: N-myc mRNA forms RNA—RNA duplex with endogenous antisense transcripts. Mol. Cell Biol. 10: 4180, 1990; Taylor E. R. et al.: Identification of antisense transcripts of the chicken insulin-like growth factor-II gene. J. Mol. Endocrinol. 7: 145, 1991).

Finally, it is also known that in most follicular B cell lymphomas, positives for t(14–18) translocation, the early events truncate the 3' end of bcl-2 gene in chromosome 18 and join it to the truncated 5' end of the IgH locus in chromosome 14, originating the chimeric gene bcl-2/IgH responsible for BCL-2 overexpression (Nunez G. et al.: Deregulated bcl-2 gene expression selectively prolongs survival of growth factor—deprived haemopoietic cell lines. J Immunol 144: 3602, 1990. Cleary M. L. et al.: Cloning and structural analysis of cDNAs for Bcl-2 and a hybrid Bcl-2/immunoglobulin transcript resulting from the t(14;18) translocation. Cell 47: 19, 1986). Protein BCL-2 has been shown to inhibit programmed cell death in certain circumstances, providing a cell survival advantage.

The bcl-2 sequence is known (Cleary M. L. et al.: Cloning and structural analysis of cDNAs for Bcl-2 and a hybrid Bcl-2/immunoglobulin transcript resulting from the t(14;18) translocation. Cell 47: 19, 1986). It is also known that its breakpoints are mainly in the 3'UTR. More particularly, about 60% of breakpoints in the chromosome 18 occurs in a segment between the nucleotide 2890 and nucleotide 3200 (major breakpoint or mbr; M. Kneba et al., Cancer Research 51, 3243–50, 1991) and 20% in a region located about 20 Kb downstream of mbr, mcr (minor breakpoint region).

In turn, the sequence of IgH locus has been also described and it is known that its breakpoints are located within one of the J regions whose sequence is known (Ravetch J. V. et al.: Structure of the human immunoglobulin locus: characterization of embryonic and rearranged J and D genes. Cell 27: 583, 1981).

For example, in the DOHH2 cells, the bcl-2 gene breaks at nucleotide 3110 and joins the segment $J_6$ of the rearranged gene of the immunoglobulin (Kluin Nelemans H. C. et al.: A new non-Hodgkin's B-cell line (DOHH2) with a chromosomal translocation t(14;18)(q32;q21). Leukemia 5: 221, 1991). Associated to this translocation, there is an insertion of 15 nucleotides (region N) between the 3' of bcl-2 and the segment $J_6$ that represents an unique and specific nucleotides sequence of DOHH2 (Nunez G. et al.: Deregulated bcl-2 gene expression selectively prolongs survival of growth factor-deprived haemopoietic cell lines. J Immunol 144: 3602, 1990. Kluin Nelemans H. C. et al.: A new non-Hodgkin's B-cell line (DOHH2) with a chromosomal translocation t(14;18)(q32;q21). Leukemia 5: 221, 1991).

The scheme of t(14–18) translocation of DOHH2-2 is shown in FIG. 1 where

A) is the scheme of the genes involved in the t(14–18); the breakpoints are indicated by dashed lines, B) is the hybrid gene bcl-2/IgH, C) is the nucleotide sequence (SEQ ID NO: 48) of the N region (CCC TGG TTC CCC GA) (SEQ ID NO: 1).

Moreover, in FIG. 1, E indicates the enhancer region. Its sequence is deposited in the EMBL Data Library Accession number X54,712 and has been published by Sun Z. et al. ("Sequencing of selected regions of the human immunoglobulin heavy-chain gene locus that completes the sequence from $J_h$ through the delta constant region. DNA sequence J DNA sequencing and mapping 1: 347,1991).

In DHL-4 cell line, (Cleary M. L. et al.: Detection of a second t(14–18) breakpoint cluster region in human follicular lymphomas. J Exp Med 164: 315, 1986. Cleary M. L. et al.: Nucleotide sequence of a t(14;18) chromosomal breakpoint in follicular lymphoma and demonstration of a breakpoint cluster region near a transcriptionally active locus on chromosome 18. Proc Natl Acad Sci USA 82: 7439, 1985) the bcl-2 gene breaks at nucleotide 2694 and joins the segment $J_4$ of the rearranged gene of the immunoglobulin. Following the translocation, 6 nucleotides (region N) are inserted between the 3' end of bcl-2 and the $J_4$ and they represent an unique sequence specific only of DHL-4 cell line.

In FIG. 1 is shown the scheme of the t(14–18) translocation in DHL-4:

A) is the scheme of genes involved in the t(14–18) translocation; the breakpoints are indicated by dashed lines, B) is the hybrid bcl-2/IgH gene, C) is the scheme of the hybrid bcl-2/IgH gene in the DHL-4 cell line with the nucleotide sequence (SEQ ID NO: 49) of the N region (CCG AGC).

In the case of K422 (Dyer M. J. et al.: A new human B-cell non Hodgkin's lymphoma cell line (Karpas 422) exhibiting both t(14;18) and t(4;11) chromosomal translocation. Brood 75: 709, 1990) the bcl-2 gene breaks within the mbr and joins a segment J of the rearranged IgH.

In the follicular lymphoma JNL(Cleary M. L. et al.: PNS 82: 7439, 1985) the bcl-2 gene breaks at nucleotide 3059 and joins the segment $J_4$ of the IgH.

In the DHL-6(Cleary M. L et al.: Cell 41: 899, 1985) the bcl-2 gene breaks at nucleotide 3139 and joins the segment $J_6$ during the IgH rearrangement.

Further examples of cell lines t(14;18) positive have been described by Tsujimoto Y., Science 229:1390,1985. In particular:

In FL1032 the bcl-2 gene breaks at nucleotide 3107 and joins the segment $J_4$ of IgH with the insertion of 18 nucleotides (N region: GTG CGT GGT TGA TGG GGA) (SEQ ID NO: 2) between the 3' end of the bcl-2 and the $J_4$ (unique sequence strictly specific of FL1032);

In FL966 the bcl-2 gene breaks at nucleotide 3110 and joins the segment $J_4$ of IgH with the insertion of 1 nucleotide (N region: C) between the 3' end of the bcl-2 and the $J_4$;

In FL1144 the bcl-2 gene breaks at nucleotide 3157 and joins the segment $J_6$ of IgH with the insertion of 11 nucleotides (N region: CCC GAG TGA AG) (SEQ ID NO: 3) between the 3' end of bcl-2 and the $J_6$ (unique sequence strictly specific of FL1144 );

In FL1003 the bcl-2 gene breaks at nucleotide 3046 and joins the segment $J_6$ of IgH with the insertion of 3 nucleotides (N region: CGA) between the 3' end of bcl-2 and the $J_6$ (unique sequence strictly specific of FL1003 ).

Now, we have found a hybrid bcl-2/IgH antisense transcript in the t(14;18) cell lines. The antisense RNA originates in the enhancer region of the IgH, encompasses the t(14;18) fusion site and spans the complete 3' region of the bcl-2 RNA.

The 3' terminal region of the bcl-2 gene, transcribed but not translated, is rich in sequences AU and AUUUA that bind site of destabilizing factors (nucleases) (Caput D. et al.: Identification of a common nucleotide sequence in the 3' untraslated region of mRNA molecules specifying inflammatory mediators. Proc. Natl. Acad. Sci. USA 83: 1670, 1986).

The chimeric bcl-2/IgH antisense transcript hybridizes with this region by masking the AU-rich elements to the destabilizing factors and thereby increasing the level of mRNA.

This causes upregulation of the BCL-2 protein expression that, by preventing programmed cell death (apoptosis), causes a neoplastic transformation.

In fact, the BCL-2 protein, located in the internal membrane of mitochondria and in the endoplasmatic reticula, prevents programmed cell death providing a cell survival advantage and a subsequent immortalization/transformation (Zutter M. et al.: Immunolocalization of the Bcl-2 protein within hematopoietic neoplasms. Blood 78: 1062, 1991. Jacobson M. D. et al.: Bcl-2 blocks apoptosis in cells lacking mitochondria DNA. Nature 361: 365, 1993). Apoptosis plays a role extremely important in situations either normal or pathologic, included the development and the differentiation of the immune and nervous systems (Cohen J. J. et al.: Apoptosis and programmed cell death in immunity. Ann. Rev. Immunol. 10: 267, 1992. Garcia I. et al.: Prevention of programmed cell death of sympathetic neurons by the Bcl-2 proto-oncogene. Science 258: 302, 1992). Recent studies showed that neoplastic cells with overproduction of BCL-2 protein are more resistant to antitumor compounds. (Miyashita T. et al.: Bcl-2 oncoprotein blocks chemotherapy-induced apoptosis in a human leukemia cell line. Blood 81: 151, 1993. Walton M. I. et al.: Constitutive expression of human Bcl-2 modulates nitrogen mustard and camptothecin induced apoptosis. Cancer Res 53: 1853, 1993).

The finding by the inventors of an endogenous antisense bcl-2/IgH transcript, that complements the immature hybrid mRNA expressed by the t(14;18) positive cells, is very important because its sequence is easily deducible from that of the correspondent immature mRNA.

In turn, the knowledge of the sequence of the antisense chimeric transcript bcl-2/IgH allows to design and synthesize, according to conventional techniques well known to the person skilled in the art, ODN capable of hybridizing with the antisense transcript and of destabilizing the same, thus inhibiting the production of BCL-2 protein and causing the cell death.

It is therefore a first object of this invention to provide a chimeric bcl-2/IgH antisense transcript that hybridizes with the pre-mRNA of a hybrid gene in t(14;18) translocated cells.

Figure 2:
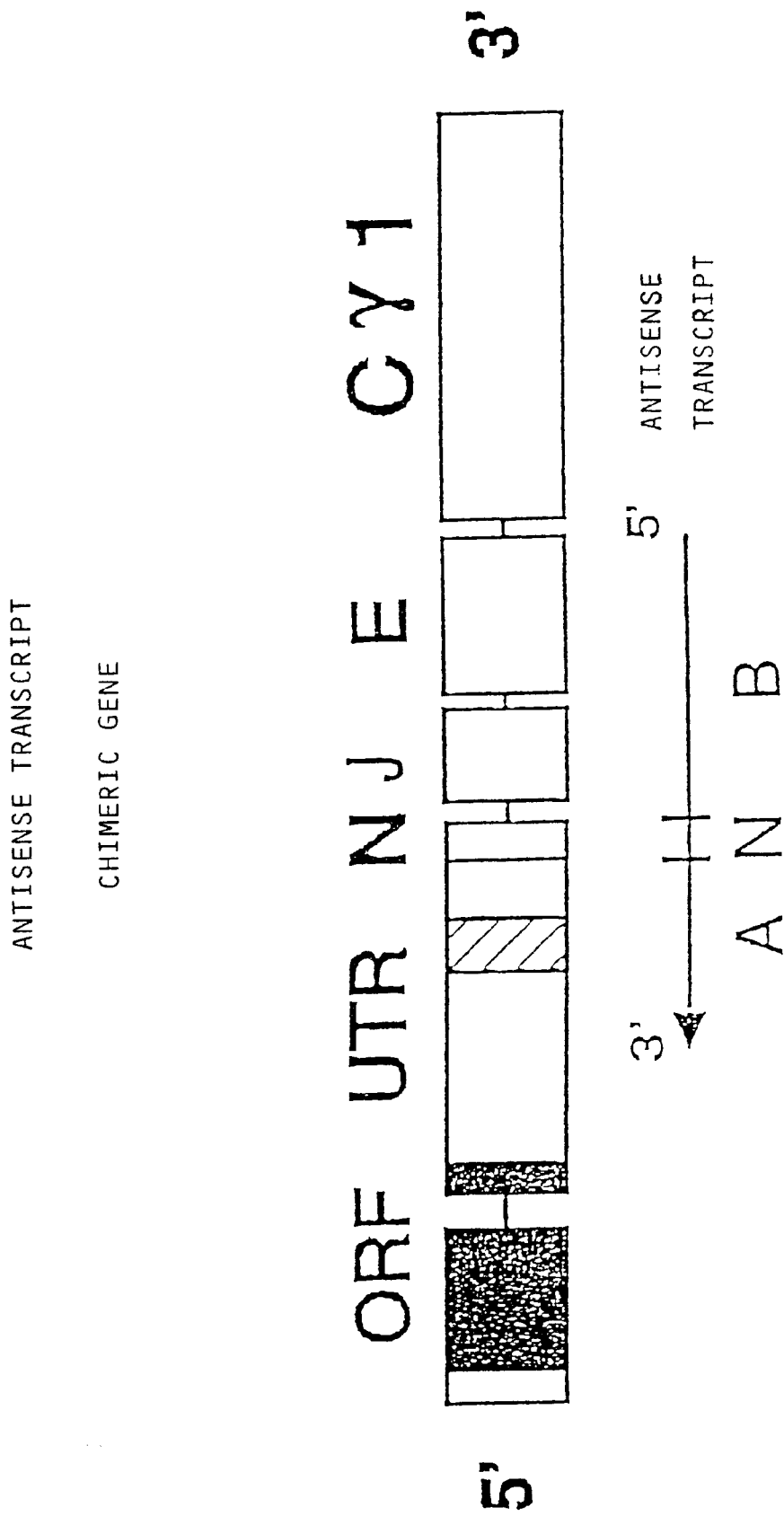

The structure of said antisense transcript may be represented by the following formula:

$$3'\text{-}A\text{-}N\text{-}B5' \qquad (\text{FIG. 2})$$

where

A is a nucleotide sequence complementary to the 3' region of bcl-2 within the hybrid bcl-2/IgH pre-mRNA, B is a nucleotide sequence complementary to the J and E (enhancer) regions of the 5' hybrid pre-mRNA bcl-2/IgH, and N is the nucleotide sequence complementary to the N region of the hybrid bcl-2/IgH pre-mRNA.

A second object of the present invention is to provide a sense oriented ODN, optionally modified in order to improve its activity in vivo, according to claims 3 to 9.

These ODNs can be directed to complement either the J region or the enhancer region of the chimeric bcl-2/IgH RNA.

Typical examples of ODNs directed to the N region of DOHH2 comprise the following sequences (SEQ ID NOS: 4–6, respectively):

CCC CGA ATA CTA CTA CTA;

TCC CTG GTT CCC CGA ATA; or

CGA ATA CTA CTA CTA CTA.

Typical examples of ODNs directed to the $J_6$ region of the immunoglobulin locus comprise the following sequences (SEQ ID NOS: 7–9, respectively):

ACT ACT ACG GTA TGG ACG (from nucleotide 2956 to nucleotide 2973);

TCC TCA GGT AAG AAT GGC (from nucleotide 3003 to nucleotide 3020); or

ACC ATG TTC CGA GGG GAC (from nucleotide 3119 to nucleotide 3136).

Useless to say that the activity of the latter ODNs will not be restricted to the immature mRNA of the DOHH2 cells; they act on the immature mRNA of any (14;18) translocated cell line.

Typical examples of ODNs directed to complement the region between $J_6$ and Enhancer ($J_6$/E) comprise the following sequences (SEQ ID NOS: 10–13, respectively):

GAG CCA CAT TTG GAC GAG (from nucleotide 3272 to nucleotide 3289);

AGT GAT GGC TGA GGA ATG (from nucleotide 3314 to nucleotide 3331);

CTG TCC AAG TAT TTG AAA (from nucleotide 3776 to nucleotide 3783); or

GGC TGG AAA GAG AAC TGT (from nucleotide 3459 to nucleotide 3476).

Even these ODNs will act not only on the immature mRNA of DOHH-2 cells; they act on the immature mRNA of any (14;18) translocated cell line.

Typical examples of ODNs directed to the 3' end of bcl-2 comprise the following sequences (SEQ ID NOS: 14–15, respectively):

GTG AGC AAA GGT GAT CGT (from nucleotide 2625 to nucleotide 2642); or

CTT CAA AAC CAT TCT GAG (from nucleotide 2672 to nucleotide 2689).

Even these ODNs will be act not only act on the chimeric antisense transcript bcl-2/IgH of DOHH-2; they act on the pre-mRNA bcl-2/IgH of any t(14;18) positive cell line wherein the bcl-2 region comprise the above mentioned nucleotides.

Typical examples of ODNs directed to the peculiar fusion region (N region) of the DHL-4 cells comprise the following sequences (SEQ ID NOS: 16–17, respectively):

GGT CCG AGC TTG ACT ACT; or

TGA GAA GGT CCG AGC TTG.

In the present description and in the claims attached hereto, the expression "modified in order to improve the in vivo activity" means those chemical modifications which are known to the person skilled in the art to increase the crossing of the cellular membranes and/or to improve the ODNs stability to the attacks of the endo and exonucleases without affecting their capability of hybridizing the target compound (Uhlmann E. et al.: Antisense oligonucleotides: a new therapeutic principle. Chemical Rev 90: 544, 1990).

Typical examples of structural modifications capable of increasing the stability to nucleases are those performed on the phosphate group. For instance, methylphosphonates, phosphoroamidates, phosphorotriesters, phosphorothioates and the phosphorodithioates.

Typical examples of chemical modifications that increase the membrane crossing are those performed with lipophilic compounds, preferably cholesterol, that usually are covalently linked via a methylene bridge (at the 5' or at the 3' termination or both).

ODNs of the present invention can be easily prepared in solid phase by means of techniques well known to the person skilled in the art, such as those reported by Narang A. (Tetrahedron 39: 3, 1983), by Itakura K. (Synthesis and use of synthetic oligonucleotides. Ann Rev Biochem 53: 323 1984), or in "Oligonucleotides Synthesis; A Pratical Approach", Gait M. J. Ed. IRL Press, Oxford, UK, 1984).

If desired, the thus prepared ODNs may be purified by conventional techniques such as, for instance, Polyacrilamide Gel Electrophoresis (PAGE) under denaturing conditions, High Performance Liquid Chromatography (HPLC) either in inverse phase or in ion-exchange column, and capillary chromatography.

The ODNs of the present invention will be dispensed to human beings by administration routes and dosages which are selected according parameters well known to the person skilled in the art depending on the disease severity, the body weight, the specific ODN which is used, and the like.

In particular, they will allow very distinctive therapies devoid of significant toxic effects, thus reaching a really important goal, i.e. a specific therapy of a well defined kind of cancer without affecting those cells that do not carry the genomic alteration of interest.

However, depending on the selected ODN, it is also possible to utilize an ODN which is complementary to not individual regions of the antisense transcript (outside the N region), thus allowing to use only one or a limited number of ODNs in the treatment of all the t(14;18) tumors.

They can be used also for diagnostic purposes allowing an extremely sensible and precise diagnosis, much better than the current methods.

Moreover, the ODNs of the present invention allow an accurate monitoring of the ongoing therapeutic treatments.

The following examples are given to better illustrate the present invention without, however, limiting it in any way.

EXAMPLE 1

Antisense Transcript Identification in t(14:18) Human Follicular B Cell Lymphoma Total RNA extracted from DOHH-2 cells, was divided in two vials and reverse transcribed by using in the vial A a primer in the antisense orientation (primer A (SEQ ID NO: 18): 5'-GGT GAC CGT GGT CCC TTG CCC CCA-3', from nucleotide 2973 to nucleotide 2998 of the $J_{H6}$) and in the vial B a primer in the sense orientation (primer B (SEQ ID NO: 19): 5'-GAC CTT GTT TCT TGA AGG TTT CCT CT CCC-3' from nucleotide 2832 to nucleotide 2862 of the bcl-2 cDNA).

The same procedure was used in t(14;18) negative B cell lymphoma Raji and in the T cell leukemia JURKAT.

The preparations of cDNA have being amplified by adding primer B to the vial A reverse transcribed with primer A and by adding primer A to the vial B where the reverse transcription had been carried out with primer B.

The amplification products were analyzed by agarose gel electrophoresis.

Figure 3:
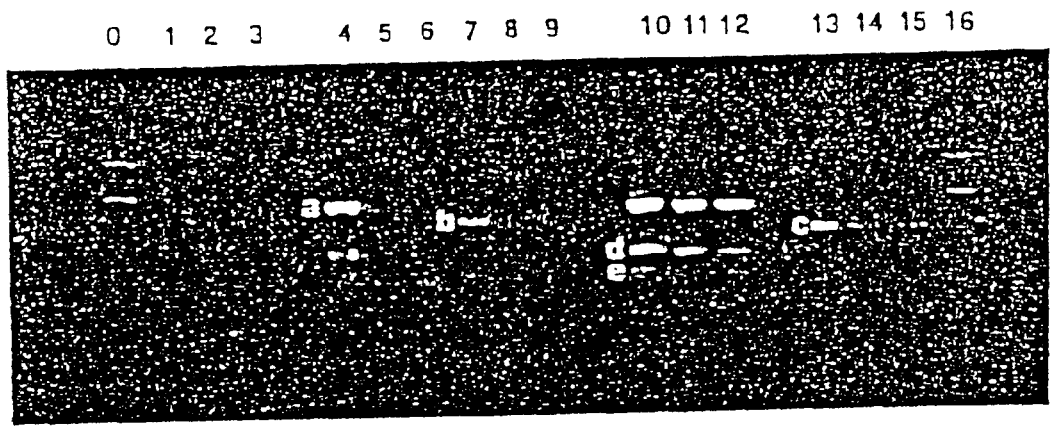

As shown in FIG. 3, DOHH2 is characterized by 2 bands in the gel, the first one about 340 bp (line 4) long, corresponding to the regular bcl-2/IgH sense transcript (primer A), the second one, about 250 bp long, corresponding to the hybrid antisense transcript (line7 primer B).

No amplification products were obtained from Raji cells (lines 5–6) and from Jurkat cells (lines 6–9) providing evidence that the t(14;18) negative cell lines carry the relevant nucleotide sequences in different chromosomes.

In order to exclude that the sense and the antisense signals were not obtained from contaminating genomic DNA, an aliquot of each RNA preparation was digested by the enzyme RNase before the reverse transcription (lines 1–3). Another aliquot of RNA was reverse transcribed with random hexamers (RH) and amplified with primers B and C (primer C (SEQ ID NO: 20): 5'-GCA CCA CTG CAT TTC AGG AAG ACC CTG AAG-3' from nucleotide 3081 to nucleotide 3110 of the bcl-2 cDNA) complementary to the bcl-2 mRNA upstream of the breakpoint (lines 10–12).

As a further control, the beta-actin RNA was amplified (primer D (SEQ ID NO: 21): 5'-GCG GGA AAT CGT CGG TGA CAT T-3' from nucleotide 2104 to nucleotide 2124 of the beta-actin cDNA, and primer E (SEQ ID NO: 22): 5'-GAT GGA GTT GAA GGT AGG GGT TTC GTG-3' from nucleotide 2409 to nucleotide 2435 of the beta-actin cDNA) from three cell lines (lines 13–15).

The same experimental procedure was repeated by using two primers (SEQ ID NOS: 23–24, respectively) both located in 3'UTR of bcl-2 (5'-GAC CTT GTT TCT TGA AGG TTT CCT CGT CCC-3' from nucleotide 2832 to 2862, and 5'-GCA CCA CTG CAT TTC AGG AAG ACC CTG AAG-3' from nucleotide 3081 to 3110) to confirm that the expression of the antisense transcript is restricted to the t(14;18) positive cell lines.

EXAMPLE 2

ODNs Preparation

The preparation was performed according to the chemistry of the beta-cyanoethyl-phosphoroamidates in solid phase with a Perkin-Elmer ABI 392 synthesizer.

Upon removal from the resin, the oligodeoxynucleotide was deprotected with 30% ammonia in 12 hours at 55° C.

Purification was carried out on a chromatography column NAP 25 (Sephadex G25) from Pharmacia Biotech.

The column NAP 25 had been balanced with 4×5 ml of 20% ethanol buffer and the crude ODN was eluted with 20% ethanol buffer.

The eluted fraction was collected and dried after spectrofluorimetric determination (at 260 and 280 nm) of the concentration.

With this procedure were prepared the following ODNs of the invention (SEQ ID NOS: 4–17, respectively):

CCC CGA ATA CTA CTA CTA
TCC CTG GTT CCC CGA ATA
CGA ATA CTA CTA CTA CTA
ACT ACT ACG GTA TGG ACG
TCC TCA GGT AAG AAT GGC
ACC ATG TTC CGA GGG GAC
GAG CCA CAT TTG GAC GAG
AGT GAT GGC TGA GGA ATG
CTG TCC AAG TAT TTG AAA
GGC TGG AAA GAG AAC TGT
GTG AGC AAA GGT GAT CGT
CTT CAA AAC CAT TCT GAG
GGT CCG AGC TTG ACT ACT
TGA GAA GGT CCG AGC TTG as well as the following primers (SEQ ID NOS: 18–22, respectively):

5'-GGT GAC CGT GGT CCC TTG CCC CCA-3'
5'-GAC CTT GTT TCT TGA AGG TTT CCT CGT CCC-3'
5'-GCA CCA CTG CAT TTC AGG AAG ACC CTG AAG-3'
5'-GCG GGA AAT CGT CGG TGA CAT T-3'
5'-GAT GGA GTT GAA GGT AGG GGT TTC GTG-3' and the following control ODNs (SEQ ID NOS: 25–40, respectively)

TAT TCG GGG AAC CAG GGA
TAG TAG TAG TAT TCG GGG
ATA AGC CCC TTG GTC CCT
CGT CCA TAC CGT AGT AGT
GCC ATT CTU ACC TGA GGA
CGA ACC GGG ATG GAC TTC
CTC GTC CAA ATG TGG CTC
ACA GTT CTC TTT CCA GCC
GAG CAG GTT TAC ACC GAG
ACG ATC ACC TTT GCT CAC
CTC AGA ATG CTT TTG AAG
AGC GAT GGT CGT GTG AAA
AGT AGT CAA GCT CGG ACC
CAA GCT CGG ACC TTC TCA
TCA TCA GUT CGA GCC TGG
GTC CCC TCG GAA CAT GGT

EXAMPLE 3

ODNs in vitro Activity Against t(14;18) Human Follicular B Cell Lymphomas

A) DOHH2

A1) ODNs biological activity

The DOHH2 was maintained in culture in RPMI added with 10% FCS (fetal calf serum), antibiotics (penicillin and streptomycin), and glutamine and incubated at 37° C. in a moist atmosphere of $CO_2$ and 95% of humidity. Before treatment with the ODNs, the cell line was washed twice with HBSS to completely remove FCS and then resuspended in complete RPMI with FCS scomplemented at 65° C. to remove the nucleases that degrade the ODN. The cells were seeded $10^4$ per well (96 microwell flat bottom) and treated at day 0 with 10 $\mu$M or with 1 $\mu$M and day 1 and day 2 with half a dose of the following ODNs of the present invention:

Group 1(SEQ ID NOS: 4–6, respectively) (ODNs complementary to the N region of the DOHH2 bcl-2/IgH mRNA)

ODN 70   CCC CGA ATA CTA CTA CTA

ODN 72   TCC CTG GTT CCC CGA ATA

ODN 73   CGA ATA CTA CTA CTA CTA

Group 2(SEQ ID NOS: 7–13, respectively) (ODNs complementary to the J6 or to the J6/E region of the IgH mRNA)

ODN 96   ACT ACT ACG GTA TGG ACG
         (from nucleotide 2956 to nucleotide 2973)

ODN 97   TCC TCA GGT AAG AAT GGC
         (from nucleotide 3003 to nucleotide 3020)

ODN 98   ACC ATG TTC CGA GGG GAC
         (from nucleotide 3119 to nucleotide 3136)

ODN 104  GAG CCA CAT TTG GAC GAG
         (from nucleotide 3272 to nucleotide 3289)

ODN 105  AGT GAT GGC TGA GGA ATG
         (from nucleotide 3314 to nucleotide 3331)

ODN 106  CTG TCC AAG TAT TTG AAA
         (from nucleotide 3776 to nucleotide 3783)

ODN 107  GGC TGG AAA GAG AAC TGT
         (from nucleotide 3459 to nucleotide 3476)

Group 3(SEQ ID NOS: 14–15, respectively) (ODNs complementary to the 3' end of the bcl-2 mRNA)

ODN 91   GTG AGC AAA GGT GAT CGT

ODN 90   CTT CAA AAC CAT TCT GAG

Moreover the DOHH2 cells have been treated with the following control ODNs:

TAT TCG GGG AAC CAG GGA
(ODN 76=antisense of ODN 72)
TAG TAG TAG TAT TCG GGG
(ODN 78=antisense of ODN 70)
ATA AGC CCC UTG GTC CCT
(ODN 75=ODN 72 inverted)
CGT CCA TAC CGT AGT AGT
(ODN 102=antisense of ODN 96)
GCC ATT CTU ACC TGA GGA
(ODN 103=antisense of ODN 97)
CGA ACC GGG ATG GAC TTC
(ODN 100=ODN 98 scramble)
CTC GTC CAA ATG TGG CTC
(ODN 120=antisense of ODN 104)
ACA GTT CTC TTT CCA GCC
(ODN 108=antisense of ODN 107)
GAG CAG GTT TAC ACC GAG
(ODN 121=ODN 104 inverted)
ACG ATC ACC TTT GCT CAC
(ODN 94=antisense of ODN 91)
CTC AGA ATG CTT TTG AAG
(ODN 93=antisense of ODN 90)
AGC GAT GGT CGT GTG AAA
(ODN 101=ODN 91 scramble)
GTC CCC TCG GAA CAT GGT
(ODN 99=antisense from ODN 98)

The inhibition of the BCL-2 protein synthesis was evaluated both by observing at the microscope the morphology of the cells treated with the ODNs of the present invention as compared with the morphology of the cells treated with the control ODNs (the apoptotic cells show a smaller cellular volume and a typical babbling of the cytoplasmic membrane), and by counting viable cells by the Trypan Blue exclusion assay followed by counting the $^3$H -Thymidine incorporation ($^3$H -Thymidine 1 mC/ml).

The cellular count and the $^3$H -Thymidine incorporation assay in the untreated cells and in cells treated with the ODNs of Groups 1, 2, and 3, in the sense or antisense orientation, are shown in Table 1. The assays have been carried out in triplicate and the data were normalized from 5 experiments.

TABLE 1

Growth inhibition of DOHH2 cells

| ODN | cells × 10$^4$/ml | $^3$H-TdR cpm × 10$^3$ |
|---|---|---|
| Control | 146 | 199 |
| Group 1 | 86 | 83 |
| Antisense Group 1 | 161 | 173 |
| Group2 | 95 | 96 |
| Antisense Group 2 | 155 | 162 |
| Group 3 | 76 | 82 |
| Antisense Group 3 | 149 | 165 |

These data show that the ODNs of the present invention strongly decrease both the cell number or the quantity of radioactivity incorporated in the cellular nuclei.

The same ODNs of the present invention were added to t(14;18) negative cell lines (K562, Jurkat, LCL, Raji) and to t(14;18) positive cell lines (DHL-4 and K422) that displays private nucleotide sequence in the N region.

No ODN of the present invention exhibited biological activity in the t(14;18) negative cell lines. In contrast, the ODNs of Groups 2 and 3 exhibited biological activity. Moreover, the ODNs of Group1, which are complementary-to the DOHH2 N region, were completely inactive.

A2) Determination of bcl-2 mRNA

The cells were exposed to the ODNs of Groups 1, 2, and 3, and to control ODNs for three days at 10 $\mu$M and 1 $\mu$M to quantitate the hybrid bcl-2/IgH mRNA level expressed in the cells by the semi-quantitative Reverse Transcriptase Polymerase Chain Reaction (RT-PCR) according to the method described by Horikoshi T. et al.: (Quantitation of Thymidylate Synthase, Dihydrofolate reductase and DT-diaphorAse gene expression in human tumors using polymerase chain reaction. Cancer Res 52: 108, 1992).

Thereafter, total cellular RNA was extracted by the RNA-zol B method (CINNA BIOTECX; Houston, Tex.), treated with Dnase and proteinase K and then reverse transcribed to cDNA with Mo-MLV reverse transcriptase (PROMEGA, Madison Wis.) and random hexamers (RX). The cDNA was amplified by PCR in the presence of radioactive ATP, AmpliTaq polymerase (PERKIN-ELMER, Norwalk, Conn.), using increased amounts of cDNA and the following primers from GENOSIS, Cambridge, England:

$\beta_2$mA (SEQ ID NO: 41), 5'-AAC CCC ACT GAA AAA GAT GA-3', from nucleotide 1544 to 1563 of the $\beta_2$ m gene;

$\beta_2$mB (SEQ ID NO: 42), 5'-ATC TTC AAA CCT CCA TGA TG-3', from nucleotide 2253 to 2262 of the $\beta_2$ m gene [Noonan K. E. et al.: Quantitative analysis of MDRI (multidrug resistance) gene expression in human tumors by polymerase chain reaction. Proc Natl Acad Sci USA, 87: 7160, 1990];

bcl-2/J$_{H6}$A (SEQ ID NO: 43), 5'-GGT GAC CGT GGT CCC TTG CCC CCA G-3', from nucleotide 2973 to 2997 of the J$_{H6}$ (Cleary M. L. et al.: Cloning and structural analysis of cDNAs for Bcl-2 and a hybrid Bcl-2/immuno globulin transcript resulting from the t(14;18) translocation. Cell 47: 19, 1986);

bcl-2/J$_{H6}$B (SEQ ID NO: 44), 5'-GCA ATT CCG CAT TTA ATT CAT GGT ATT CAG GAT-3', from nucleotide 2866 to 2898 of the bcl-2 gene.

After 30 cycles of PCR, the amplified products were quantitated by counting the radioactivity in the bands excised from the 6% PAGE under non-denaturing conditions, dissolved in the scintillation liquid.

The samples were also analyzed by the 1.5% agarose gel electrophoresis and quantitated by densitometry.

The amount of the hybrid bcl-2/IgH RNA was calculated by comparison with the internal standard $\beta$-actin and $\beta_2$ microglobulin.

The obtained data, calculated as percentage of the untreated control, show that the ODNs of the present invention caused a decrease in the content of the chimeric mRNA in a dose dependent fashion, both at 10 $\mu$M or at 1 $\mu$M. The cells treated with control ODNs did not display any variation in the content of hybrid mRNA.

Moreover, the bcl-2 mRNA has been quantitated in other t(14;18) positive cell lines (DOHH-2, DHL-4 and K422) that express private nucleotide sequence in the fusion site and with the K562 cell line which is negative to t(14;18), after treatment with the ODNs of Group 3.

A marked reduction of the mRNA amount in the three t(14;18) positive cell lines was observed. In contrast no mRNA variation was observed in the K562 cells.

A3) Protein BCL-2 determination

The amount of BCL-2 protein was also evaluated in the cell samples treated with the ODNs of the Groups 1, 2 and 3, and with control ODNs as well.

The BCL-2 protein in the cells has been determined by flow cytometry (Aiello A. et al.: Flow cytometric detection of the mitochondrial BCL-2 protein in normal and neoplastic human lymphoid cells. Cytometry 13: 502, 1992).

In particular, pelleted cells fixed in 2% paraformaldehyde, have been treated with Anti-BCL-2 MoAb (Pezzella. F. et al.: Expression of the Bcl-2 oncogenic protein is not specific for the t(14;18) chromosomal translocation. Am J Pathol 137: 225, 1990) and normal mouse serum as negative control to detect the autofluorescence. After several washings, the cells were analyzed by flow cytometry using an EPICS-C instrument (COULTER ELECTRONICS, Hialeah, Fla.) equipped with an argon-ion laser.

The cells treated with the ODNs of the Groups 1, 2, and 3 showed a reduced BCL-2 protein level as compared with the fluorescence intensity in the untreated cells or in cells treated with control ODNs.

T(14;18) negative tumor cell lines treated with the ODNs of the present invention or with the control ODNs did not show any variation in the BCL-2 protein level.

The ODNs of the present invention hybridize with the antisense transcript that originates in the IgH locus, encompasses the t(14;18) fusion site and spans at least the complete 3' UTR region of bcl-2 mRNA, they are thus capable of inhibiting the antisense transcript overexpression of the BCL-2 protein. Consequently, the destabilizing region in the 3' end of the bcl-2 gene may be exposed to the negative regulatory elements and the destabilization of mRNA causes a reduction in the level of the BCL-2 protein.

B) DHL-4

B1) Biological activity of the ODNs

Figure 4:
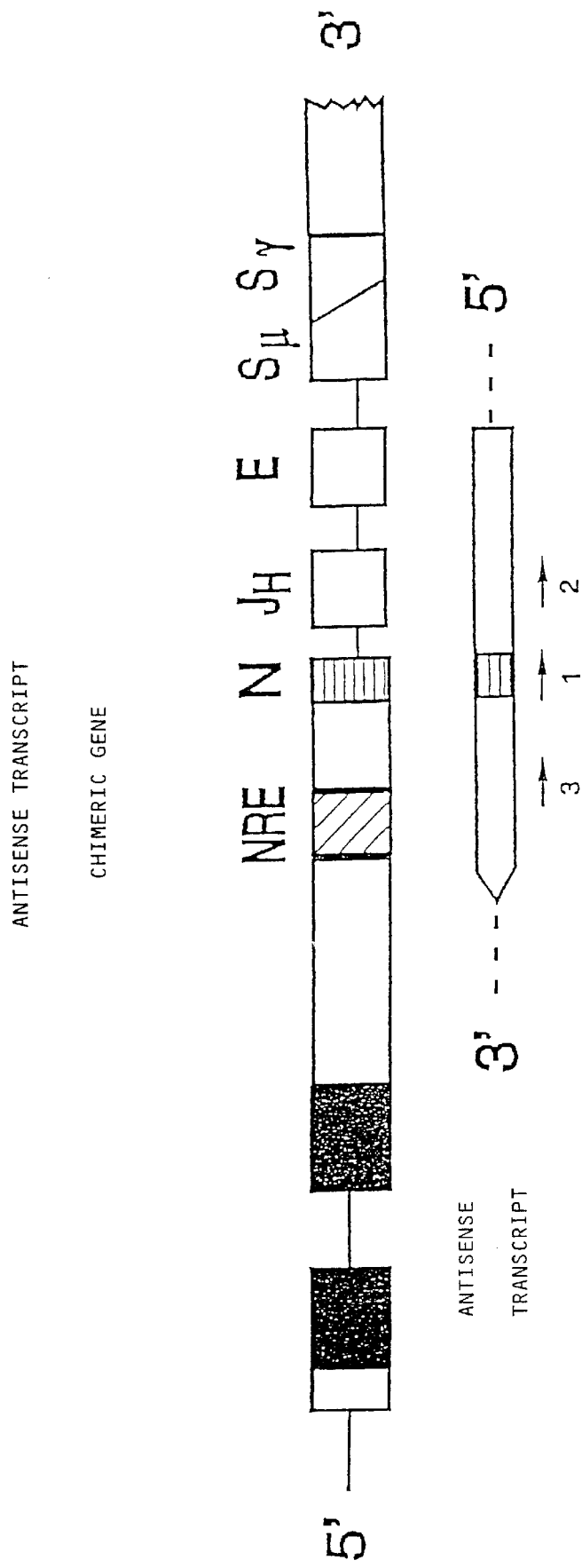

There were used the the above mentioned ODNs of the Groups 2 and 3, the corresponding control ODNs, the following ODNs complementary to the N region of the DHL-4 cell line (FIG. 4) (SEQ ID NOS: 16–17, respectively):

```
(ODN 56)    GGT CCG AGC TTG ACT ACT
(ODN 55)    TGA GAA GGT CCG AGC TTG
``` and the following control ODN (SEQ ID NOS: 45–47, respectively):

AGT AGT CAA GCT CGG ACC
(ODN 58=antisense of ODN 56)
CAA GCT CGG ACC TTC TCA
(ODN 54=antisense of ODN 55)
TCA TCA GTT CGA GCC TGG
(ODN 59=inverted ODN 56)

The experiments were carried out as described in the example 3A1.

The experimental results show that the ODNs of Group 2, acting at the nuclear level, hybridize with the segment $J_6$ present in the chimeric pre mRNA of the DHL4 and inhibit DHL4 growth. The ODNs of Group 3, targeting the 3' end of the bcl-2 mRNA segment within the chimeric mRNA, cause a similar DHL-4 growth inhibition.

It follows that the ODNs of Groups 2 and 3 are active on all the t(14;18) positive cell lines irrespective of the peculiar nucleotide sequence of the fusion region.

B2) Protein BCL-2 determination

Working in a similar manner as disclosed in Example 3A3 above, the ODNs of the present invention caused a reduction. The amount of the BCL-2 protein expressed in the cells has been carried out as described in the example 3A3.

Therefore, since they act on any region of the antisense transcript of any t(14;18) positive cell lines, the ODNs of the present invention decrease the intracellular amount of the BCL-2 protein and induce the apoptotic cell death.

EXAMPLE 4

Apoptosis Determination

Cellular DNA fragmentation, in addiction to cellular morphologic alterations, is a peculiar property of apoptosis.

After exposure of the DOHH2, DHL-4 and K422 cell lines to the above mentioned ODNs of Groups 2 and 3, and to the corresponding control ODNs, the nuclear DNA fragmentation has been evaluated by cytofluorimetry (Delia D. et al.: N-(4-Hydroxyphenyl)retinamide induces apoptosis of malignant haemopoietic cell lines including those unresponsive to retinoic acid. Cancer Res. 53: 6036, 1993).

This method is based on the binding of the fluorescinated deoxyuridine to the 3'-OH end which originates from DNA fragmentation. This reaction is catalyzed by the enzyme TdT (Terminal desoxytransferase) (Gavrieli Y. et al.: Identification of programmed cell death in situ via specific labeling of nuclear DNA fragmentation. J Cell Biol 119: 493, 1992). The incorporation of the fluorescinated nucleotide is quantitated by flow-cytometry.

The cells, whether treated or untreated, were fixed 10 min. in 2% paraformaldehyde, washed twice in 0.1M Tris (pH 7.2), fixed again in acetone for 1 min., washed again and incubated with the enzyme TdT (BOERINGHER Mannheim) and fluorescinated UTP for 1 hour at 37° C. After 2 washes the cells were analyzed at the flow-cytometer.

It was found an increased fluorescence in all the t(14;18) positive cell lines as compared with the same cell lines untreated or treated with control ODNs.

Therefore the ODNs of the present invention, complementary to any region of the antisense transcript, are capable of inhibiting the action of the antisense transcript and of inducing the death of the t(14;18) positive cell lines.

EXAMPLE 5

In vivo Activity of ODN Against The t(14:18) Human Follicular B Cell Lymphomas

Preliminary, it was studied the growth of the DOHH2 lymphoma in immunodeficient mice (SCID). Immunodeficiency is an autosomic spontaneous recessive mutation on chromosome 16 responsible for an alteration in the, recombinant system which controls the correct rearrangement of the VDJ loci both in T and in B lymphocytes. The SCID mice lost the B and T functions while the Natural Killer activity is inactivated by antibodies to the asyalglicoprotein. Therefore in these mouse strains the transplantation of human tumors is successful.

The take of the DOHH2 follicular lymphoma injected iv in these mice was confirmed. Then studies have initiated to evaluate the therapeutic activity of a sense oriented ODN of this invention (ODN 72).

Four mice carrying the above mentioned lymphoma were treated from day 1 to day 15 with 1 mg/day of said ODN.

A 4 animals control group carrying the same lymphoma was treated in the same way with the corresponding antisense oriented ODN (ODN 76).

A further 4 animals group carrying the same lymphoma was treated with physiological solution (untreated controls).

The treatment with the above mentioned ODNs and the physiological solution was performed by an osmotic micropump (ALZET, Charles River) inserted subcutaneously to each mouse and containing the compounds under evaluation. The pump released 1 mg/day for a total or 15 mg/mouse.

In the group of animals treated with ODN 72 it was obtained an increase in the average survival time.

We claim:

1. An isolated, full-length chimeric bcl-2/IgH antisense transcript that hybridizes with the pre-mRNA of a hybrid gene in t(14;18) translocated cells.

2. The chimeric bcl-2/IgH antisense transcript according to claim 1, characterized by the formula:

3'-A-N-B5' where

A is a nucleotide sequence complementary to the 3' region of bcl-2 within the hybrid bcl-2/IgH pre-mRNA, B is a nucleotide sequence complementary to the J and E (enhancer) regions of the 5' hybrid pre-mRNA bcl-2/IgH, and N is the nucleotide sequence complementary to the N region of the hybrid bcl-2/IgH pre-mRNA.

3. An ODN, optionally modified in order to improve its activity in vivo, which may have up to 100 base pairs and is directed to complement the J6 region of a immunoglobulin within a chimeric bcl-2/IgH antisense transcript which hybridizes with the pre-MRNA of a hybrid gene having a t(14;18) translocation, thus inhibiting the action thereof.

4. An ODN according to claim 3 which, comprises a sequence of the formula:

ACT ACT ACG GTA TGG ACG (SEQ ID NO: 7);
TCC TCA GGT AAG AAT GGC (SEQ ID NO: 8); or
ACC ATG TTC CGA GGG GAC (SEQ ID NO: 9).

5. An ODN, optionally modified in order to improve its activity in vivo, which may have up to 100 base pairs and is directed to complement the J6/E region of an immunoglobulin within a chimeric bcl-2/IgH antisense transcript which hybridizes with the pre-MRNA of a hybrid gene having a t(14;18) translocation, thus inhibiting the action thereof.

6. An ODN according to claim 5 which comprises a sequence of the formula:

GAG CCA CAT TTG GAC GAG (SEQ ID NO: 10);
AGT GAT GGC TGA GGA ATG (SEQ ID NO: 11);
CTG TCC AAG TAT TTG AAA (SEQ ID NO: 12); or
GGC TGG AAA GAG AAC TGT (SEQ ID NO: 13).

7. An ODN, optionally modified in order to improve its activity in vivo, which may have up to 100 base pairs and is directed to complement the 3' end of bcl-2 within a chimeric bcl-2/IgH antisense transcript which hybridizes with the pre-MRNA of a hybrid gene, having a t(14;18) translocation, thus inhibiting the action thereof.

8. An ODN according to claim 7 which comprises a sequence of the formula:

GTG AGC AAA GGT GAT CGT (SEQ ID NO: 14); or
ACT CAA AAC CAT TCT GAG (SEQ ID NO: 15).

9. A pharmaceutical composition for treating a t(14,18) tumor, comprising (a) a therapeutically effective dose of an ODN, optionally modified in order to improve its activity in vivo, which may have up to 100 base pairs and is directed to complement the J6 region of an immunoglobulin within a chimeric bcl-2/IgH antisense transcript which hybridizes with the pre-MRNA of a hybrid gene having a t(14,18) translocation, thus inhibiting the action thereof, and (b) a pharmaceutically acceptable carrier.

10. A pharmaceutical composition according to claim 9, wherein said ODN comprises a sequence of the formula:

ACT ACT ACG GTA TGG ACG; (SEQ ID NO: 7)
TCC TCA GGT AAG AAT GGC (SEQ ID NO: 8); or
ACC ATG TTC CGA GGG GAC (SEQ ID NO: 9).

11. A pharmaceutical composition for treating a t(14,18) tumor, comprising (a) a therapeutically effective dose of an ODN, optionally modified in order to improve its activity in vivo, which may have up to 100 base pairs and is directed to complement the J6/E region of an immunoglobulin within a chimeric bcl-2/IgH antisense transcript which hybridizes with the pre-MRNA of a hybrid gene having a t(14,18) translocation, thus inhibiting the action thereof, and (b) a pharmaceutically acceptable carrier.

12. A pharmaceutical composition according to claim 11, wherein said ODN comprises a sequence of the formula:

GAG CCA CAT TTG GAC GAG (SEQ ID NO: 19);
AGT GAT GGC TGA GGA ATG (SEQ ID NO: 11);
CTG TCC AAG TAT TTG AAA (SEQ ID NO: 12); or
GGC TGG AAA GAG AAC TGT (SEQ ID NO: 13).

13. A pharmaceutical composition for treating a t(14,18) tumor, comprising (a) a therapeutically effective dose of an ODN, optionally modified in order to improve its activity in vivo, which may have up to 100 base pairs and is directed to complement the 3' end of bcl-2 within a chimeric bcl-2/IgH antisense transcript which hybridizes with the pre-MRNA of a hybrid gene having a t(14,18) translocation, thus inhibiting the action thereof, and (b) a pharmaceutically acceptable carrier.

14. A pharmaceutical composition according to claim 13, wherein said ODN comprises a sequence of the formula:

GTG AGC AAA GGT GAT CGT (SEQ ID NO: 14); or
CTT CAA AAC CAT TCT GAG (SEQ ID NO: 15).

* * * * *